United States Patent [19]
Thakrar

[11] Patent Number: 6,099,926
[45] Date of Patent: Aug. 8, 2000

[54] ALIPHATIC POLYKETONE COMPOSITIONS AND MEDICAL DEVICES

[75] Inventor: Ashok R. Thakrar, San Jose, Calif.

[73] Assignee: Intella Interventional Systems, Inc., Sunnyvale, Calif.

[21] Appl. No.: 08/989,791

[22] Filed: Dec. 12, 1997

[51] Int. Cl.[7] ...................................................... A61L 29/00
[52] U.S. Cl. ................... 428/36.92; 428/35.2; 428/35.5; 428/35.7; 428/36.9; 604/96; 604/101; 604/508; 604/525; 604/919; 606/108; 606/192; 606/194; 607/119
[58] Field of Search ................................. 428/35.7, 35.2, 428/36.9, 35.5, 36.92; 604/96, 101, 919, 508, 525; 606/108, 192, 194; 608/119

[56] References Cited

U.S. PATENT DOCUMENTS

| | | | |
|---|---|---|---|
| Re. 32,983 | 7/1989 | Levy | 428/36.92 |
| Re. 33,561 | 3/1991 | Levy | 428/36.92 |
| 4,490,421 | 12/1984 | Levy | 428/35 |
| 4,744,366 | 5/1988 | Jang | 128/344 |
| 4,880,904 | 11/1989 | Kinneberg et al. | 528/392 |
| 5,055,024 | 10/1991 | Jackowski et al. | 425/140 |
| 5,213,574 | 5/1993 | Tucker | 604/93 |
| 5,232,786 | 8/1993 | Waters et al. | 428/475.8 |
| 5,270,086 | 12/1993 | Hamlin | 428/35.2 |
| 5,281,200 | 1/1994 | Corso, Jr. et al. | 604/96 |
| 5,300,085 | 4/1994 | Yock | 606/191 |
| 5,438,988 | 8/1995 | Duan et al. | 128/640 |
| 5,531,690 | 7/1996 | Solar | 604/102 |
| 5,554,121 | 9/1996 | Ainsworth et al. | 604/96 |
| 5,556,383 | 9/1996 | Wang et al. | 604/96 |
| 5,567,203 | 10/1996 | Euteneuer et al. | 604/96 |
| 5,569,199 | 10/1996 | Solar | 604/96 |
| 5,569,201 | 10/1996 | Burns | 604/96 |
| 5,607,406 | 3/1997 | Hernandez et al. | 604/264 |
| 5,849,846 | 12/1999 | Chen et al. | 525/166 |
| 5,891,114 | 4/1999 | Chien et al. | 604/282 |

FOREIGN PATENT DOCUMENTS

| | | |
|---|---|---|
| 0 171 884 A1 | 2/1986 | European Pat. Off. . |
| 0 745 395 A2 | 12/1996 | European Pat. Off. . |
| WO 94/05361 | 3/1994 | WIPO . |
| WO 95 15780 | 6/1995 | WIPO . |
| WO 95 23619 | 9/1995 | WIPO . |
| WO 96 03162A1 | 2/1996 | WIPO . |
| WO 98/54261 | 12/1998 | WIPO . |
| WO 98/54262 | 12/1998 | WIPO . |

OTHER PUBLICATIONS

Shell Chemical Company, "Carilon Polymers—Discover a New Generation of Building Blocks" (1996).

Danforth, R.L., et al.; Aliphatic Polyketones–A New Family of Engineering Thermoplastics; Mar. 1996; Plastics Engineering; pp. 77–79.

*Primary Examiner*—Ellis Robinson
*Assistant Examiner*—John Figueroa

[57] ABSTRACT

Disclosed are medical devices of aliphatic polyketone polymers and/or polyketone polymer compositions comprising at least one aliphatic polyketone and at least one plasticizer. Also disclosed are polyketone compositions that comprise at least one aliphatic polyketone and at least one plasticizer.

20 Claims, No Drawings

ALIPHATIC POLYKETONE COMPOSITIONS AND MEDICAL DEVICES

BACKGROUND OF THE INVENTION

1. Field of the Invention

The present invention relates to polyketone polymers and compositions. More particularly, the invention relates to medical devices made using polyketone polymers and compositions.

2. Description of Related Art

Polymers are often materials of choice for use in medical devices. For example, polyethylenes, polyurethanes, polyesters, and nylons have been used in a variety of medical devices, such as catheters and PTCA balloons.

However, polymeric materials in use today suffer from a number of disadvantages. For example, such materials may suffer from relatively high coefficients of friction, rendering intraluminal applications undesirably difficult. Additionally, several common polymeric materials are brittle, such that the frequent bending and flexing required in medical devices may cause these materials to fail prematurely. Furthermore, other common polymeric materials may not be biocompatible, making their use in medical devices unsafe and possibly illegal.

There is a need, therefore, for a suitable polymeric material, compositions that contain the polymeric material, and medical devices that comprise the material and or the compositions, that solve the aforementioned problems.

SUMMARY OF THE INVENTION

This invention relate to a composition comprising at least one aliphatic polyketone and at least one plasticizer. This invention additionally relates to a medical device comprising polyketone polymer or a composition of at least one aliphatic polyketone and at least one plasticizer.

DETAILED DESCRIPTION OF THE INVENTION

In one aspect, this invention relates to a composition comprising at least one aliphatic polyketone and at least one plasticizer. The invention also relates to the composition wherein the plasticizer comprises aromatic sulfonamide, aromatic phosphate ester, alkyl phosphate ester, alkyl ester, citrate ester, butyl benzosulfonamide, acetate, adipate, amide, azelate, epoxide, glutarate, N,N-dimethyl caprylamide capramide, N,N-dimethyl oleamide, epoxidized glycol dioleate, or analogs or derivatives or mixtures thereof. The invention also relates to the composition further comprising customary additives and processing aids. The invention also relates to the composition wherein the total amount of plasticizers, additives and other materials comprises less than about 20 weight percent based on the total composition weight.

In another aspect, the invention concerns a medical device comprising an aliphatic polyketone polymer or a composition of at least one aliphatic polyketone and at least one plasticizer. The invention also relates to the medical device wherein the plasticizer comprises aromatic sulfonamide, aromatic phosphate ester, alkyl phosphate ester, alkyl ester, citrate ester, butyl benzosulfonamide, acetate, adipate, amide, azelate, epoxide, glutarate, N,N-dimethyl caprylamide capramide, N,N-dimethyl oleamide, epoxidized glycol dioleate, or analogs or derivatives or mixtures thereof. The invention also relates to the medical device further comprising customary additives and processing aids. The invention also relates to the medical device wherein the total amount of plasticizers, additives and other materials comprises less than about 20 weight percent of based on the total composition weight.

In another aspect, the invention relates to the medical device wherein the medical device is minimally invasive. The invention also relates to such a device wherein the plasticizer comprises aromatic sulfonamide, aromatic phosphate ester, alkyl phosphate ester, alkyl ester, citrate ester, butyl benzosulfonamide, acetate, adipate, amide, azelate, epoxide, glutarate, N,N-dimethyl caprylamide capramide, N,N-dimethyl oleamide, epoxidized glycol dioleate, or analogs or derivatives or mixtures thereof. The invention also relates to the medical device further comprising customary additives and processing aids. The invention also relates to the medical device wherein the total amount of plasticizers, additives and other materials comprises less than about 20 weight percent of based on the total composition weight.

In yet another aspect, the invention concerns a medical device where the medical device comprises a percutaneous and non-intraluminal device. The invention also relates to the medical device wherein the plasticizer comprises aromatic sulfonamide, aromatic phosphate ester, alkyl phosphate ester, alkyl ester, citrate ester, butyl benzosulfonamide, acetate, adipate, amide, azelate, epoxide, glutarate, N,N-dimethyl caprylamide capramide, N,N-dimethyl oleamide, epoxidized glycol dioleate, or analogs or derivatives or mixtures thereof. The invention also relates to the medical device further comprising customary additives and processing aids. The invention also relates to the medical device wherein the total amount of plasticizers, additives and other materials comprises less than about 20 weight percent of based on the total composition weight.

Additionally, the invention concerns a medical device wherein the medical device comprises an intraluminal tubular member. The invention also relates to the medical device wherein the plasticizer comprises aromatic sulfonamide, aromatic phosphate ester, alkyl phosphate ester, alkyl ester, citrate ester, butyl benzosulfonamide, acetate, adipate, amide, azelate, epoxide, glutarate, N,N-dimethyl caprylamide capramide, N,N-dimethyl oleamide, epoxidized glycol dioleate, or analogs or derivatives or mixtures thereof.

The invention also relates to the medical device further comprising customary additives and processing aids. The invention also relates to the medical device wherein the total amount of plasticizers, additives and other materials comprises less than about 20 weight percent of based on the total composition weight. The invention also relates to the medical device where the medical device comprises a percutaneous and non-intraluminal device. The invention also relates to the medical device where the medical device comprises an intravascular catheter. The invention also relates to the medical device where the medical device comprises an intracornoary catheter. The invention also relates to the medical device where the medical device comprises a percutaneous device. The invention also relates to the medical device where the medical device comprises a non-percutaneous device.

Further, the invention concerns a medical device where the medical device comprises an intraluminal balloon. The invention also relates to the medical device wherein the plasticizer comprises aromatic sulfonamide, aromatic phosphate ester, alkyl phosphate ester, alkyl ester, citrate ester, butyl benzosulfonamide, acetate, adipate, amide, azelate, epoxide, glutarate, N,N-dimethyl caprylamide capramide, N,N-dimethyl oleamide, epoxidized glycol dioleate, or analogs or derivatives or mixtures thereof. The invention also relates to the medical device further comprising customary additives and processing aids. The invention also relates to the medical device wherein the total amount of plasticizers, additives and other materials comprises less than about 20 weight percent of based on the total composition weight. The invention also relates to the medical device where the medical device comprises a percutaneous device. The invention also relates to the medical device where the medical device comprises a non-percutaneous device. The invention also relates to the medical device where the medical device comprises a single balloon. The invention also relates to the medical device where the medical device comprises multiple balloons. The invention also relates to the medical device wherein the balloon wall material is biaxially oriented. The invention also relates to the medical device wherein the balloon is about 1.5 to 12 mm in diameter. The invention also relates to the medical device wherein the balloon is capable of deploying a stent. The invention also relates to the medical device wherein the balloon is semi-compliant. The invention also relates to the medical device wherein the balloon wall material is perforated or is sufficiently porous to permit drug delivery through the wall material.

Polyketones are a relatively newly developed class of polymers. Therefore, polyketone polymers and compositions have not been previously utilized for medical device applications. After much research, however, the inventor has unexpectedly discovered that the properties of polyketone polymers and compositions make them outstanding materials of construction for medical devices. This is because of desirable properties, including reasonable biocompatibility, good processability, good dimensional stability, and good tensile strength and elongation. Additionally, polyketone polymers and compositions can be utilized in a startlingly broad range of medical devices. This is because of properties such as low coefficient of friction, excellent bondability to other medical device materials, excellent hydrolytic stability, and an easily tailorable Young's modulus. These properties allow a medical device designer considerable latitude in selecting the appropriate polyketone polymer or composition to meet design needs. In particular, polyketone polymers and compositions may be advantageously used in medical devices, including but not limited to, inflatable balloons and catheter shafts.

The aliphatic polyketones used in this invention are generally derived from carbon monoxide and alpha olefins. Such polyketones are generally thermoplastic in nature, and may be characterized as strong, tough, and ductile polymers. Specific polyketone polymers are available from Shell Chemical Company (Houston, Tex.) under the trademark CARILON®. Typical properties for aliphatic polyketones may be:

| | |
|---|---|
| Specific Gravity | 1.24 |
| Tensile Strength @ yield, psi | 8,700–9,200 |
| Elongation @ yield % | 22–28 |
| @ break | 300 |
| Tensile Modulus, psi | 230,000 |
| Flexural Modulus, psi | 220,000 |
| Wear Factor | 215 × 10-10 in$^3$-min/lb-ft-hr |
| Melting Point Deg. F. | 428 |

The properties of the aliphatic polyketone polymers used in this invention may be improved by using plasticizers. Plasticizers are materials that may be added to polymeric materials primarily to improve flexibility. In addition, plasticizers may reduce melt viscosity and lower the glass transition temperature of the polymeric materials. By varying the level of plasticizer, it may be possible to vary the final properties of the plasticized polymeric material. Plasticizers usable with aliphatic polyketones in the present invention generally are polar.

Examples of plasticizers include, but are not limited to aromatic sulfonamides, aromatic phosphate esters, alkyl phosphate esters, alkyl esters, citrate esters, butyl benzosulfonamides, acetate, adipate, amides, azelates, epoxides, glutarates such as polyester glutarate, N,N-dimethyl caprylamide capramide, N,N-dimethyl oleamide, epoxidized glycol dioleate, and analogs and derivatives and mixtures thereof.

The plasticizers used in this invention are known to one of skill in the art and are readily available from conventional suppliers. For example, citrate esters are derived from citric acids, generally have benign toxicology, and are available as CITROFLEX® from Morflex, Inc (Greensboro, N.C.). Butyl benzosulfamides generally are light yellow liquids, having a pleasant odor, and are available as PLASTHALL® from the C. P. Hall Company (Chicago, Ill.). Further discussion of suitable plasticizers can be found in *Modern Plastics Encyclopedia,* C-99–108 (1997). This document is incorporated by reference in its entirety as if reproduced completely herein, as are all documents specifically cited herein.

Additional additives may be used in the course of practicing the invention. Examples of such additives are processing aids such as stearates, low molecular weight waxes, titanium and/or zirconium coupling agents, antioxidants. Other customary additives may also be added. These additives may be added with or without adding a plasticizer, and may be added separately or in combination.

Compounding the aliphatic polyketones and plasticizers and/or additives according to the invention can be done according to methods known in the art. Such methods are generally described in *Two Phase Polymer Systems,* 69–91 (1991)(L. a. Utracki, ed.). The polyketone polymer may be compatible with a limited quantity of plasticizers or additives. Excessive use of plasticizer or additives may lead to blooming or leaching of the plasticizer or additive and/or phase separation. Preferred amounts of plasticizers incorporated into the plasticized aliphatic polyketones compositions according to the invention range from about 0.01 to about 20 weight percent on the total composition weight, preferably from about 5 to about 20 weight percent on the total composition weight. Other additives or materials compounded with the polyketones may be included in a preferred amount of about zero to about five weight percent on the total composition weight, more preferably from about 0.01 to about 5 weight percent on the total composition weight. Preferably, the total amount of plasticizers, additives and other materials is less than about 20 weight percent of based on the total composition weight.

Conventional methods for making polymeric medical devices can be easily adapted by one of skill in the art to making medical devices from the polyketone polymers and compositions of the present invention. This is because the polyketone polymers and compositions according to the invention can be worked using techniques that are conventional in the polymer art. In particular, catheter balloons having oriented wall materials of polyketone polymer and composition can be made according to the general teachings of Levy, U.S. Pat. No. Re 33,561, and Jackowski et al, U.S. Pat. No. 5,055,024.

The polyketone polymers and compositions can be used to make a variety of medical devices, as noted above. Generally speaking, polyketone polymers and compositions can be used with existing medical device architectures, or can be used to create entirely new devices based on the superior properties of polyketone polymers and compositions. For example, polyketone polymers and compositions can be used in conventional intraluminal catheters shafts, replacing polyethylene or polyurethane. Alternatively, polyketone polymers and compositions may be used to create surgical tools and implements. In a proper formulation, polyketone polymers or compositions may even be able to be used in long-term implant devices, such as stents, pacemakers, or bone or cartilage replacements. In a preferred embodiment, the inventive polyketone polymers and compositions can be used to create balloon catheters having balloons with improved properties. More preferably, such balloon catheters according to the invention are semi-compliant.

An example of this is illustrated by the combination of known multiple balloon catheter architectures with polyketone polymers and compositions. In Jang, U.S. Pat. No. 4,744,366, a multiple balloon catheter architecture is disclosed. The term multiple balloon is used herein to mean more than one balloon. The materials of construction disclosed for use as catheter balloon materials are polyvinyl chloride, polyester, and polyethylene, can be advantageously substituted with the inventive polyketone polymers or compositions. Such a substitution may result in balloons with lower coefficients of friction and improved folding properties, thus enhancing the balloon's and overall catheter system's performance.

Other known medical device architectures may be adapted for use with polyketone polymers and compositions according to the invention. For example Corso, Jr. et al. (U.S. Pat. No. 5,281,200), Yock (U.S. Pat. No. 5,300,085), Solar (U.S. Pat. No. 5,531,690), Euteneuer et al. (U.S. Pat. No. 5,567,203), Solar (U.S. Pat. No. 5,569,199), Burns (U.S. Pat. No. 5,569,201), and Hernandez et al. (U.S. Pat. No. 5,607,406) all disclose structures that may be adapted for use with the present invention, using polymer techniques well known in the art.

EXAMPLES

Physical properties of polyketone polymer and compositions according to the invention were compared with conventional medical device materials, particularly polyester and plasticized nylon. The tests were performed on both standard test pieces and sample balloons according to the following procedures.

The tensile property of the balloons were measured using a Chatilon tensile tester model TCD 200. In this procedure, one end of the cylindrical part of the balloon was attached to the lower jaw and the other end was attached to the upper jaw which was then attached to a load cell. The distance between the two jaws was measured and the sample was pulled at 0.5 inch/minute until torn. Total deflection and the force gauge reading were recorded. The tensile property of the tested balloon and its elongation were calculated as follows:

Tensile Strength=Force/(Double Wall thickness/2)*PI*Diameter of the Balloon % Elongation={(Final length−Original length)/ Original length}*100

The coefficient of friction was measured for catheter shafts by wrapping the sample catheter shaft a full 360 degrees around a pulley made out of polyacetal material. A known tension (T1) was placed at the one end of the catheter shaft and the catheter shaft was pulled from the other end. The resulting dynamic tension (T2) was measured using a Chatilon tensile tester. The coefficient of friction was calculated using the following equation:

$$f=\beta ln(T2/T1)$$

where f=coefficient of friction
$\beta$=angle of tension T1 and T2
T1=known tension at the bottom of the shaft
T2=dynamic tension Stiffness of the catheter shafts were tested using a three point bending method where an approximately 2 inch long piece of a shaft was deflected on a supported beam under the action of a centrally located point load. The ratio of deflection to sample length was less than or equal to 0.06. Using the following equation the stiffness and modulus of elasticity were calculated.

$$\delta=(F.L^3)/(48.EI)=(F.L^3)/(48.Sb) \text{ Hence, } Sb=EI=(F.L^3)/(48.\delta)$$

$\delta$=deflection, mm
Sb=bending stiffness of the sample in N-mm$^2$
F=force applied, Newtons
L=length, mm
E=modulus of elasticity, N/mm$^2$
I=moment of inertia, Ix=Iy of the beam X section about the neutral axis, mm$^4$ Balloon burst tests were carried out using a Crescent Design's Hydraulic Burst-Leak Tester Model 100, according to the manufacturer's instructions.

EXAMPLE 1

A molding composition of 89 weight percent of aliphatic polyketone CARILON® R-1000 (available from Shell Chemical Company) was prepared by plasticizing using 11 weight percent butyl benzosulfonamide (available as PLAS-THALL® from C. P. Hall Company). The composition was compounded on a 27 mm Leistritz twin screw extruder, using a conventional homogenizing screw design. The screw speed was 345 RPM and the melt temperature was 250° C. The extruded blend was pelletized and collected. This blend was then re-extruded into a 0.019/0.038" ID/OD tube using a 25 mm single screw extruder. The barrel temperature ranged from 440 Deg. F. to 490 Deg. F. from feeding zone to the die head respectively. Test pieces, including 2.5 mm diameter balloons were prepared using conventional techniques. The test pieces were then tested, with the results as shown in Tables 1 and 2.

EXAMPLE 2

A molding composition of 90 weight percent of aliphatic polyketone CARILON® R-1000 (available from Shell Chemical Co.) was prepared by plasticizing with 10 weight percent of Triethyl Citrate (available from Moreflex as CITROFELX®). The composition was compounded on a 27 mm Leistritz twin screw extruder, using a conventional homogenizing screw design. The screw speed was 345 RPM and the melt temperature was 250° C. The extruded blend was pelletized and collected. This blend was then re-extruded into a 0.019/0.038" ID/OD tube using a 25 mm single screw extruder. The barrel temperature ranged from 440 Deg. F. to 490 Deg. F. from feeding zone to the die head respectively. Test pieces, including 2.5 mm diameter balloons were prepared using conventional techniques. The test pieces were then tested, with the results as shown in Tables 1 and 2.

EXAMPLE 3

Polyketone Resin (CARILON® R1000, available from Shell Chemical, Akron, Ohio) was extruded into a 0.019/0.038" ID/OD tube using a 25 mm single screw extruder. The barrel temperature ranged from 450 Deg. F. to 490 Deg. F. from feeding zone to the die head respectively. Test pieces, including 2.5 mm diameter balloons were prepared using conventional techniques. The test pieces were then tested, with the results as shown in Tables 1 and 2.

COMPARATIVE EXAMPLE 4

Polyester Resin (TRAYTUF® available from Shell Chemical, Akron, Ohio) was extruded into a 0.019/0.038" ID/OD tube using a 25 mm single screw extruder. The barrel temperature ranged from 520 Deg. F. to 560 Deg. F. from feeding zone to the die head respectively. Test pieces, including 2.5 mm diameter balloons were prepared using conventional techniques. The test pieces were then tested, with the results as shown in Tables 1 and 2.

COMPARATIVE EXAMPLE 5

Plasticized Polyamide resin (VESTAMID® L-2124, available from Huls America), composed of 89 wt % polyamide and 11 wt % butyl sulfonamide plasticizer was extruded into a 0.019/0.038" ID/OD tube using a 25 mm single screw extruder. The barrel temperature ranged from 420 Deg. F. to 460 Deg. F. from feeding zone to the die head respectively. Test pieces, including 2.5 mm diameter balloons were prepared using conventional techniques. The test pieces were then tested, with the results as shown in Tables 1 and 2.

EXAMPLE 6

A molding composition of 95 weight percent of aliphatic polyketone CARILON R-1000 (available from Shell Chemical Company) is prepared by plasticizing using 5 weight percent butyl benzosulfonamide (available as PLAS-THALL® from C. P. Hall Company). The composition is compounded on a 27 mm Leistritz twin screw extruder, using a conventional homogenizing screw design. The screw speed is 345 RPM and the melt temperature was 250° C. The extruded blend is pelletized and collected. This blend is then re-extruded into a 0.019/0.038" ID/OD tube using a 25 mm single screw extruder. The barrel temperature ranges from 440 Deg. F. to 490 Deg. F. from feeding zone to the die head respectively. Test pieces, including 2.5 mm diameter balloons are prepared using conventional techniques.

EXAMPLE 7

A molding composition of 95 weight percent of aliphatic polyketone CARILON R-1000 (available from Shell Chemical Co.) is prepared by plasticizing with 5 weight percent of Triethyl Citrate (available from Moreflex as CITROFELX®). The composition is compounded on a 27 mm Leistritz twin screw extruder, using a conventional homogenizing screw design. The screw speed is 345 RPM and the melt temperature was 250° C. The extruded blend is pelletized and collected. This blend is then re-extruded into a 0.019/0.038" ID/OD tube using a 25 mm single screw extruder. The barrel temperature ranges from 440 Deg. F. to 490 Deg. F. from feeding zone to the die head respectively. Test pieces, including 2.5 mm diameter balloons are prepared using conventional techniques.

TABLE 1

| Example | Balloons Properties | | | | Burst |
|---|---|---|---|---|---|
| | Coefficient of Friction | | Tensile | Elongation | Pres. |
| Numbers | IN AIR | IN WATER | psi | % | atm. |
| 1 | 0.120 | 0.090 | 19600 | 70 | 19 |
| 2 | 0.116 | 0.107 | 19200 | 59 | 18 |
| 3 | 0.100 | 0.084 | 24870 | 72 | 24 |
| 4 (Comparative) | 0.090 | 0.073 | 28000 | 50 | 27 |
| 5 (Comparative) | 0.160 | 0.110 | 17900 | 67 | 17 |

TABLE 2

| Example Numbers | Bending Stiffness N-mm2 | Young's Modulus of Elasticity N/mm2 |
|---|---|---|
| 1 | 17.6 | 1703 |
| 2 | 18.2 | 1846 |
| 3 | 23.6 | 1685 |
| 4 (Comparative) | 111.0 | 8455 |
| 5 (Comparative) | 9.9 | 1846 |

It will be apparent to those skilled in the art that various modifications and variations can be made in the devices and compositions of the present invention without departing from the spirit or scope of the invention. Thus, it is intended that the present invention cover the invention. Thus, it is intended that the present invention cover the modifications and variations of this invention provided that they come within the scope of the appended claims and their equivalents.

What is claimed is:

1. An intraluminal balloon that comprises:
   (a) at least one aliphatic polyketone; or
   (b) a composition comprising at least one aliphatic polyketone and at least one plasticizer;
   wherein the at least one aliphatic polyketone is derived from monomers consisting of carbon monoxide and alpha olefins.

2. The intraluminal balloon of claim 1, wherein the plasticizer comprises aromatic sulfonamide, aromatic phosphate ester, alkyl phosphate ester, alkyl ester, citrate ester, butyl benzosulfonamide, acetate, adipate, amide, azelate, epoxide, glutarate, N,N-dimethyl caprylamide capramide, N,N-dimethyl oleamide, epoxidized glycol dioleate, or analogs or derivatives or mixtures thereof.

3. The intraluminal balloon of claim 1, further comprising additives and other materials; wherein the total amount of plasticizers, additives and other materials comprises less than about 20 weight percent based on the total composition weight.

4. The intraluminal balloon of claim 1, wherein a wall material, of which the intraluminal balloon is comprised, is biaxially oriented.

5. The intraluminal balloon of claim 1, wherein the intraluminal balloon is about 1.5 to 12 mm in diameter.

6. The intraluminal balloon of claim 1, wherein the intraluminal balloon is semi-compliant.

7. The intraluminal balloon of claim 1, wherein a wall material, of which the intraluminal balloon is comprised, is perforated or is sufficiently porous to permit drug delivery through the wall material.

8. A minimally invasive medical device comprising the intraluminal balloon of claim 1.

9. The minimally invasive medical device of claim 8, wherein the plasticizer comprises aromatic sulfonamide, aromatic phosphate ester, alkyl phosphate ester, alkyl ester, citrate ester, butyl benzosulfonamide, acetate, adipate, amide, azelate, epoxide, glutarate, N,N-dimethyl caprylamide capramide, N,N-dimethyl oleamide, epoxidized glycol dioleate, or analogs or derivatives or mixtures thereof.

10. The minimally invasive medical device of claim 8, further comprising additives and other materials; wherein the total amount of plasticizers, additives and other materials comprises less than about 20 weight percent based on the total composition weight.

11. The minimally invasive medical device of claim 8, wherein the intraluminal balloon is capable of deploying a stent.

12. The minimally invasive medical device of claim 8, wherein the intraluminal balloon comprises an intravascular balloon.

13. The minimally invasive medical device of claim 8, wherein the intraluminal balloon comprises an intracornoary balloon.

14. The minimally invasive medical device of claim 8, wherein the minimally invasive medical device comprises a percutaneous device.

15. The minimally invasive medical device of claim 8, where the minimally invasive medical device comprises a non-percutaneous device.

16. The minimally invasive medical device of claim 8, wherein the minimally invasive medical device comprises a single intraluminal balloon.

17. The minimally invasive medical device of claim 8, wherein the minimally invasive medical device comprises multiple intraluminal balloons.

18. A minimally invasive medical device comprising an intraluminal tubular member, wherein the intraluminal tubular member comprises the intraluminal balloon of claim 1.

19. The minimally invasive medical device of claim 18, wherein the plasticizer comprises aromatic sulfonamide, aromatic phosphate ester, alkyl phosphate ester, alkyl ester, citrate ester, butyl benzosulfonamide, acetate, adipate, amide, azelate, epoxide, glutarate, N,N-dimethyl caprylamide capramide, N,N-dimethyl oleamide, epoxidized glycol dioleate, or analogs or derivatives or mixtures thereof.

20. The minimally invasive medical device of claim 18, further comprising additives and other materials; wherein the total amount of plasticizers, additives and other materials comprises less than about 20 weight percent based on the total composition weight.

\* \* \* \* \*